| United States Patent [19] | [11] | 4,203,756 |
| Gaertner | [45] | May 20, 1980 |

[54] METHOD FOR INCREASING THE SUCROSE CONTENT OF GROWING PLANTS

[75] Inventor: Van R. Gaertner, Ballwin, Mo.

[73] Assignee: Monsanto Company, St. Louis, Mo.

[21] Appl. No.: 972,540

[22] Filed: Dec. 22, 1978

[51] Int. Cl.² ............................................. A01N 5/00
[52] U.S. Cl. ........................................................ 71/86
[58] Field of Search ............................................ 71/86

[56] References Cited

U.S. PATENT DOCUMENTS

| 3,910,969 | 10/1975 | Franz | 260/397 |
| 4,035,176 | 7/1977 | Rueppel | 71/86 |
| 4,047,926 | 9/1977 | Rueppel | 71/86 |

*Primary Examiner*—Catherine L. Mills
*Attorney, Agent, or Firm*—Arnold H. Cole; Donald W. Peterson

[57] ABSTRACT

The sucrose content of sugarcane plants is increased by treating said plants, prior to harvest, with N-substituted ethylene derivatives of N-phosphonomethylglycine, and certain esters and salts thereof.

12 Claims, No Drawings

METHOD FOR INCREASING THE SUCROSE CONTENT OF GROWING PLANTS

This invention relates to a method for increasing the sucrose content of growing plants. More particularly, this invention is concerned with a method wherein sugarcane plants are subjected to a chemical treatment which serves to increase the amount of harvestable sucrose in said plants.

It is known that certain phosphonic acid compounds have been used to enhance the yield of sucrose from sugarcane plants. For example, U.S. Pat. No. 3,853,530, describes the use of N-phosphonomethylglycine, and salts, esters, amides and N-acyl derivatives thereof for this purpose. Other derivatives of N-phosphonomethylglycine are described for this use in U.S. Pat. Nos. 3,910,969, 4,035,176, 4,047,926, 4,062,669 and 4,063,922.

It has now been found that the N-substituted ethylene derivatives of N-phosphonomethylglycine, and certain salts and esters thereof, when applied to sugar producing plants in the manner hereinafter described, serve to increase the amount of recoverable sucrose in such plants. It is believed that this desirable effect results from an action of the chemical to reduce or retard further vegetative growth of the treated plant just prior to its harvest. Thus, the reducing sugars which are stored in the plant are not used as energy for plant growth but are rather converted to recoverable sucrose.

The chemical substances employed in practicing the method of this invention consist of compounds illustrated by the formula

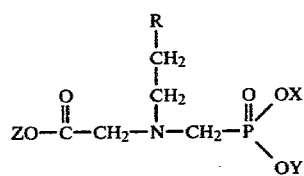

wherein R represents cyano, carbamoyl or carboxyl, X represents hydrogen or alkali metal, Y represents hydrogen, lower alkyl or phenyl, and Z represents hydrogen, lower alkyl, phenyl or alkali metal. As employed herein, lower alkyl designates saturated aliphatic hydrocarbon radicals having 1 to 4 carbon atoms in a straight or branched chain.

In general, the compounds of the present invention are prepared by reacting an alkali metal salt of N-phosphonomethylglycine or esters thereof with acrylonitrile or acrylamide. Where the desired R group is carboxyl, the reaction product is subjected to ion exchange chromatography. The examples which follow will serve to illustrate in detail the preparation of specific individual compounds of the above formula.

EXAMPLE 1

A suitable reaction vessel was charged with 16.9 grams (0.10 mole) of N-phosphonomethylglycine in 30 ml. of water and 16.0 grams (0.20 mole) of 50% aqueous sodium hydroxide with stirring and cooling at about 20° C. To the resultant solution of the disodium salt of N-phosphonomethylglycine, there was added 6.0 grams (0.11 mole) of acrylonitrile which was not soluble. After stirring overnight, partial reaction was noted by nmr, and 2 drops of a phase-transfer catalyst were added, followed by overnight rotation on a wheel. A further 6.0 grams of acrylonitrile was added, and the reaction appeared to be complete after a total of 6 days. An unchanged acrylonitrile layer which remained was separated, and the aqueous layer was acidified with concentrated HCl. The precipitate was removed by filtration, and the filtrate was rotoevaporated to dryness at <60° C./1 mm. The semi-crystalline residue was partially redissolved in a little water to leave a white crystalline solid which was separated, rinsed with water and dried. The product obtained was 8.1 grams of the monosodium salt of N-(2-cyanoethyl)-N-phosphonomethyl-glycine, m.p. 160°-200° C. (dec.). Elemental analysis showed 11.49% nitrogen and 12.81% phosphorus as against calculated values of 11.48% and 12.69% for $C_6H_{10}N_2NaO_5P$.

EXAMPLE 2

The procedure of Example 1 was followed, and after separation of the white crystalline solid, the remaining filtrate was diluted with additional water to precipitate further crops of crystals. The first crop of 4.0 grams was collected and dissolved in water with just enough sodium hydroxide to assist solubility at room temperature. The solution was then passed through an ion exchange chromatographic column in the acid form, and 50 ml. cuts 4–6 were collected and combined. The solution was concentrated to near-dryness, rediluted with water, heated and filtered to yield 1.7 grams of N-(2-carboxyethyl)-N-phosphonomethylglycine as a white powder, m.p. 207°-208° C. (dec.). Elemental analysis showed 5.81% nitrogen and 12.84% phosphorus as against calculated values of 6.44% and 12.70% for $C_6H_{12}NO_7P$.

EXAMPLE 3

A solution of the disodium salt of N-phosphonomethylglycine was prepared as described in Example 1. To a 0.05 mole portion of the solution there was added 4.0 grams (0.056 mole) of acrylamide, and the mixture was rotated on a wheel. The turbid solution which formed was permitted to stand for about 3 weeks and was then filtered through diatomaceous earth. A portion of the filtrate was evaporated to dryness at 56° C./<1 mm. to yield 2.9 grams of the disodium salt of N-(2-carbamoylethyl)-N-phosphonomethylglycine as a colorless friable glass. Elemental analysis showed 9.50% nitrogen and 10.42% phosphorus as against calculated values of 9.86% and 10.90% for $C_6H_{11}N_2Na_2O_6P$.

EXAMPLE 4

A suitable reaction vessel was charged with 2.7 grams (0.01 mole) of ethyl N-[(hydroxy)phenoxyphosphonometyl]glycinate in 10 ml. of water. The solution was cooled and treated with 0.8 grams of 50% aqueous sodium hydroxide, after which 5.0 grams (0.095 mole) of acrylonitrile was added. After 3 days, the unchanged acrylonitrile layer was removed and discarded. The aqueous layer was rotoevaporated to dryness, redissolved in a little water and treated with excess ethanol. A minor amount of precipitate which formed overnight was filtered off, and further ethanol was added to the filtrate. After 3 days the reaction mixture was concentrated to dryness and dried in a dessicator over potassium hydroxide pellets. The product, obtained as a brittle light amber glass, was 2.8 grams of the monosodium salt of ethyl N-(2-cyanoethyl)-N-phenoxyphosphonomethylglycinate. Elemental analysis showed 8.34% nitrogen and 9.43% phosphorus as against calculated values of 8.04% and 8.89% for $C_{14}H_{18}N_2NaO_5P$.

EXAMPLE 5

A suitable reaction vessel was charged with 2.0 grams of ethyl N-(hydroxy)ethoxyphosphonometylglycinate in 10 ml. of water, and the solution was treated with sodium hydroxide to bring the pH to about 8. A 2.0 grams portion of acrylonitrile was added, and the mixture was rotated on a polymer wheel. After 2 days, a turbid homogeneous mixture was present, and this was permitted to stand for about 8 weeks. It was then filtered, and the filtrate was rotoevaporated in steam at <1 mm. and dried. The product, obtained as a brittle yellow glass, was 1.2 grams of the monosodium salt of ethyl N-(2-cyanoethyl)-N-ethoxyphosphonomethylglycinate. Elemental analysis showed 39.88% carbon, 6.01% hydrogen, 9.42% nitrogen and 10.37% phosphorus as against calculated values of 40.01%, 6.04%, 9.33% and 10.32% for $C_{10}H_{18}N_2NaO_5P$.

In determining the appropriate rates and times of application to sugarcane plants, it is necessary to consider both the chronological age of the plant and its stage of maturity since cane, depending upon the practice in different geographical areas, is grown from 9 to about 30 months before harvest. Application at a rate of from about 0.11 to 5.6 kg. per hectare can be made from about 2 to 10 weeks prior to the projected harvest date. Preferably, such applications are made from 3 to 7 weeks before said date.

The active ingredients of this invention can be conveniently applied to the plants as an aqueous solution or suspension. For example, a liquid composition may be applied from a boom-spray, or a solid dust composition where the active component is diluted with an inert solid such as clay can be flown on the plants from an aircraft. Suitable liquid compositions include surfactants such as those enumerated in U.S. Pat. Nos. 3,224,865 and 3,245,775. Preferred surface active agents which are convenient to use in liquid compositions of this invention are of the non-ionic type such as alkyl phenoxypoly(ethyleneoxy)ethanols, polyethylene oxide adducts of fatty and resin acids, and long chain alkyl mercaptan adducts with ethylene oxide.

A particularly preferred carrier for the acids, esters or salts of this invention is water with about 0.1 to 2.0% by weight of surfactant added thereto. It has been found convenient to apply the compositions to the plants in the form of aqueous solutions, suspensions or emulsions, the dilution being such that a spray volume of from about 10 to 30 liters of liquid per hectare will contain the desired dosage of active ingredient. It will be recognized, however, that higher or lower total spray volumes can be beneficially employed depending upon the particular dispensing apparatus and other factors well understood by those skilled in the art.

The specific tests which follow are presented as illustrative, non-limiting demonstrations of the useful and unexpected properties of the acids, esters and salts of this invention.

Test Procedures (A) One-half gram of a compound of this invention is dissolved in 4 ml. water that contains about 0.25% (w./w.) of a non-ionic surfactant (an ethoxylated nonyl phenol). 0.6 ml. of this solution is deposited or dropped by means of a syringe with a fine needle on the spindle area at the top of the last visible dewlap of each of 20 stalks of sugarcane. (A dewlap is the junction between the blade of the leaf and the sheath which clasps the stalk). Ten of these stalks were harvested 4 weeks after such treatment and 10 more were harvested 5 weeks after such treatment.

(B) 38 mg. of a compound of this invention is added to 0.3 ml. of water or a water/solvent mixture, and a non-ionic surfactant (an ethoxylated nonyl phenol) is added in an amount of 0.1% of the final volume. This solution is deposited by means of a pipet to the whorl of 10 stalks of sugarcane. At the time of application, each stalk is marked at internode number 13. Five of these stalks are harvested 4 weeks after such treatment, and the remaining five stalks are harvested 5 weeks after such treatment.

The top 15 joints of the treated cane in procedure (A), or the top 13 joints in procedure (B), as well as those of similar but untreated cane, are removed, combined and analyzed in terms of juice purity and pol percent cane, following the so-called "press method" developed by T. Tanimoto, Hawaiian Planters Record, 57, 133 (1964). "Pol percent cane" is a polarimetric determination and equals the percentage of sucrose if the latter is the only substance in the solution which will rotate the plane of polarized light. In any event, determination of the pol percent cane is a standard and effective method for determining the sucrose content of sugarcane. The results are given below, and the procedure for each test is indicated by the appropriate letter designation.

|     |           | FOUR WEEKS      |               | FIVE WEEKS      |               |
|-----|-----------|-----------------|---------------|-----------------|---------------|
|     |           | Juice Purity    | Pol % Cane    | Juice Purity    | Pol % Cane    |
| (A) | Example 1 | 79.49           | 10.72         | 84.12           | 12.11         |
|     | Control   | 76.07           | 7.95          | 69.35           | 7.47          |
| (A) | Example 2 | 71.26           | 7.39          | 79.28           | 9.17          |
|     | Control   | 78.07           | 9.23          | 77.90           | 8.55          |
| (B) | Example 3 | 77.91           | 10.25         | 75.27           | 9.09          |
|     | Control   | 74.16           | 8.81          | 76.98           | 10.85         |
| (A) | Example 3 | 76.86           | 9.21          | 77.09           | 9.24          |
|     | Control   | 62.37           | 5.58          | 67.06           | 6.27          |
| (A) | Example 4 | 78.87           | 9.83          | 74.71           | 8.63          |
|     | Control   | 72.47           | 7.56          | 75.97           | 8.95          |

It will be understood that these test results represent procedures carried out on different dates and/or on different fields of sugarcane. Untreated control stalks were employed as the basis for comparison in each test, and the data demonstrate the improved properties on one or both of the harvest dates.

Although the invention has been described herein with respect to specific embodiments, the details thereof are not to be construed as limitations except to the extent defined in the following claims.

What is claimed is:

1. A method for increasing the sucrose content of sugarcane plants which comprises applying to said plants, from about 2 to 10 weeks prior to harvest, an effective sucrose increasing amount of a compound of the formula

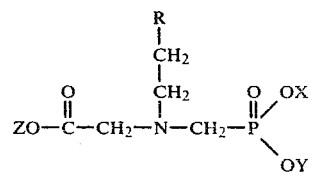

wherein R represents cyano, carbamoyl or carboxyl, X represents hydrogen or alkali metal, Y represents hydrogen, lower alkyl or phenyl, and Z represents hydrogen, lower alkyl, phenyl or alkali metal.

2. A method as defined in claim 1 wherein application is at a rate of about 0.11 to 5.6 kg. per hectare.

3. A method as defined in claim 2 wherein application is made from about 3 to 7 weeks prior to harvest.

4. A method as defined in claim 1 wherein R is cyano.

5. A method as defined in claim 4 wherein X is sodium.

6. A method as defined in claim 1 wherein R is carbamoyl.

7. A method as defined in claim 1 wherein R is carboxyl.

8. A method as defined in claim 5 wherein Y and Z are hydrogen.

9. A method as defined in claim 5 wherein Y and Z are ethyl.

10. A method as defined in claim 5 wherein Y is phenyl and Z is ethyl.

11. A method as defined in claim 6 wherein Y is hydrogen, and X and Z are sodium.

12. A method as defined in claim 7 wherein X, Y and Z are hydrogen.